United States Patent [19]
Stindt et al.

[11] 4,300,566
[45] Nov. 17, 1981

[54] CARDIAC PACER CIRCUIT

[75] Inventors: Richard E. Stindt, Coon Rapids; Thomas C. Wright, New Brighton, both of Minn.

[73] Assignee: Cardiac Pacemakers, Inc., St. Paul, Minn.

[21] Appl. No.: 89,959

[22] Filed: Oct. 31, 1979

[51] Int. Cl.³ .............................................. A61N 1/36
[52] U.S. Cl. ............................................ 128/419 PG
[58] Field of Search .................... 128/419 PG, 419 PT

[56] References Cited
U.S. PATENT DOCUMENTS

| | | | |
|---|---|---|---|
| 3,431,912 | 3/1969 | Keller, Jr. | 128/419 PG |
| 3,669,120 | 6/1972 | Nielsen | 128/419 PG |
| 3,835,865 | 9/1974 | Bowers | 128/419 PG |
| 4,023,121 | 5/1977 | Alley | 128/419 PG |
| 4,114,627 | 9/1978 | Lewyn et al. | 128/419 PT |

Primary Examiner—William E. Kamm
Attorney, Agent, or Firm—Orrin M. Haugen; Thomas J. Nikolai

[57] ABSTRACT

An electronic switching circuit for use in a demand-type cardiac pacer for (1) allowing the amplitude of the stimulating pulses to be selected, (2) ensuring a high input impedance for the heartbeat sensing amplifier, and (3) ensuring a low recovery time following the generation of a pacer pulse. Disposed between the heart contacting electrodes and the sensing amplifier is an electronic switch which is closed during a predetermined period (the sensing interval), but which is opened when the pulse generator is producing a pacer pulse. Thus, the sensing amplifier is shielded from receiving the high voltage surge occasioned by the application of a pacer pulse to the heart. Similarly, an electronic switching device is interposed between the pulse generator and the heart contacting electrodes, which device is closed during a pacing interval, but open during the aforesaid sensing interval, thus isolating the sensing amplifier from the pacer circuitry. Included in the system is a voltage doubler and associated switches which can selectively double or not double the amplitude of the stimulating pacer pulse. In either event, the charge on the voltage doubling capacitor is recovered through the heart in a relatively short time following the cessation of a pacer pulse.

1 Claim, 2 Drawing Figures

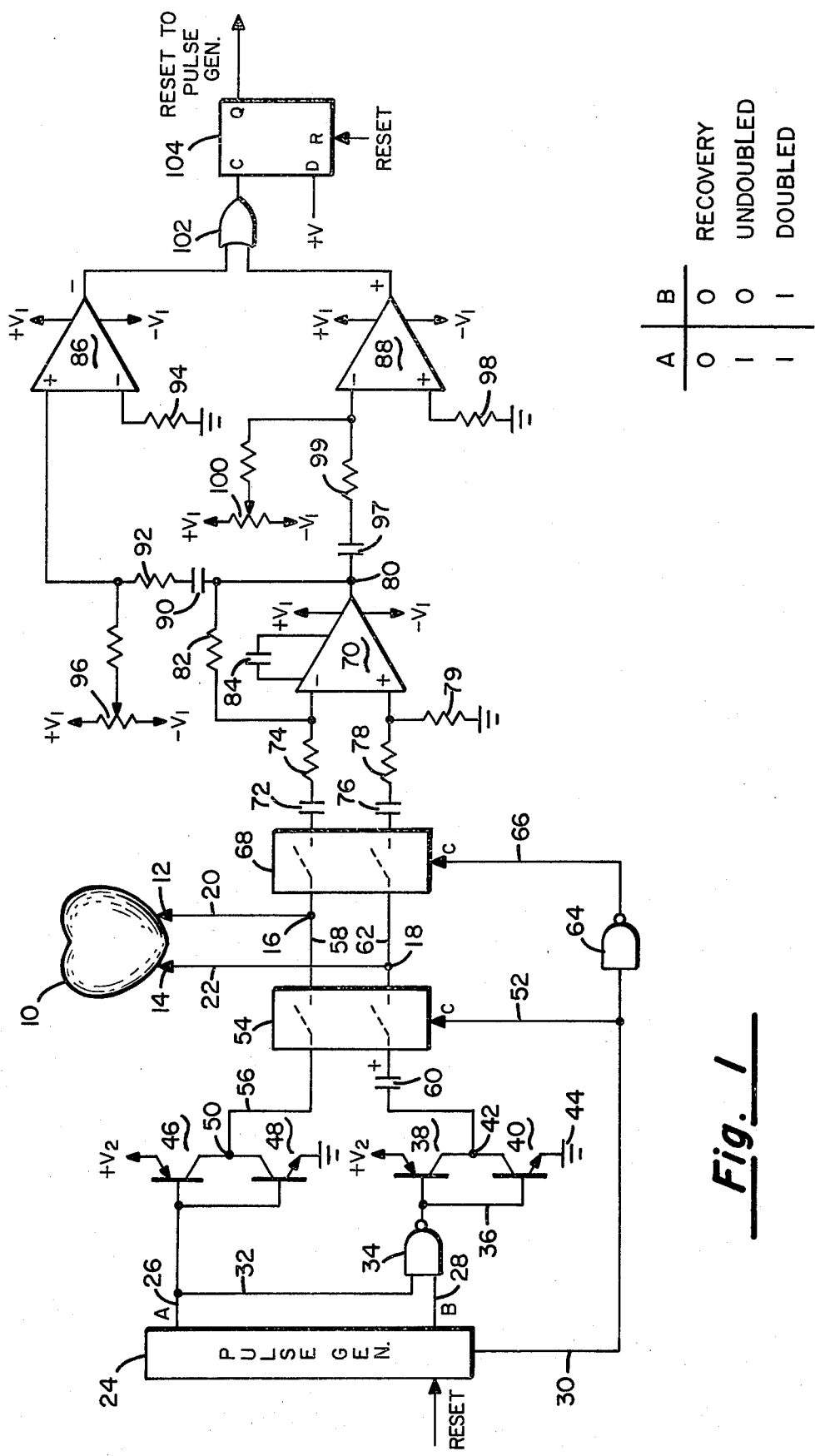

CARDIAC PACER CIRCUIT

BACKGROUND OF THE INVENTION

I. Field of the Invention

This invention relates generally to an electronic circuit for use in demand-type cardiac pacing apparatus, and more specifically to the design of a switching circuit used to selectively couple the pulse generator to the heart contacting electrodes during a pacing interval but disconnecting the pulse generator and connecting the R-wave sensing amplifier to the heart contacting electrodes during a sensing interval.

II. Discussion of the Prior Art

In demand-type cardiac pacers the circuitry functions to generate pulses at a desired rate for application to the heart of the patient only in the absence of naturally occurring heartbeat activity. The same electrodes which are utilized to apply the artificial stimulating pulses to the heart in the absence of naturally occurring heart activity are also used to pick up the electrical signals generated upon depolarization of the heart muscle and to apply these signals to the R-wave sensing amplifier, the output of which is used to inhibit or reset the pulse generator so that it does not produce artificial stimulating pulses when normal R-waves are being produced on a regular basis. To keep the size of the unit sufficiently small so that it may be implanted within the body of the patient, the number of battery cells employed is limited. To achieve artificial stimulating pulses of a sufficient amplitude to ensure capture, prior art pacer systems often employ a voltage doubler circuit which is disposed between the pulse generator output and the electrode lead terminals. Such voltage doubler circuits commonly employ an energy storing capacitor which becomes charged between pacer pulses such that at the time of occurrence of an output from the pulse generator, the voltage on the capacitor is added to the normal supply voltage to yield a resulting stimulating pulse which is approximately twice the battery potential.

Because in prior art arrangements the voltage doubling capacitor and the sensing amplifier are each coupled to the same electrode leads, difficulty has been encountered in ensuring that the energy storing capacitor is fully recharged prior to the expiration of the normal refractory period. This has been due to the fact that the charging circuit for the voltage doubling capacitor included the resistors defining the input impedance of the sense amplifier. For proper sensing without undue loading, it has been a requirement that the input impedance of the sensing amplifier be somewhere in excess of 20,000 ohms. With an effective impedance of this magnitude coupled in the charging circuit for the voltage doubler capacitor, it necessarily resulted in an inordinately large charge recovery time. Thus, the voltage difference appearing across the input of the sensing amplifier at the completion of the refractory period was sufficiently large to be interpreted by the system as a R-wave. Because of this, prior art pacer systems could have the pulse generator inhibited when, in fact, no real R-wave was being spontaneously produced by the heart muscle.

In accordance with the present invention, there is provided a unique switching mechanism which is coupled between the heart contacting electrode lead terminals, the input to the sensing amplifier and the output from the voltage doubler along with suitable control circuitry for allowing stimulation, selectively, at a first voltage or at approximately twice that voltage, while still isolating the sense amplifier from the pulse generating circuitry during a pacer pulse interval. Furthermore, the switching device of the present invention ensures that only a relatively low impedance will be connected in series between the voltage source and the voltage doubling capacitor for a predetermined period following the generation of a pacer pulse so that the capacitor becomes recharged well before the expiration of the refractory period. However, when the switching circuit is conditioned such that sensing of naturally occurring R-waves is to take place, the input impedance of the sensing amplifier is sufficiently high so as to not load down the signal source. Furthermore, the current which flows to recharge the voltage doubling capacitor following the generation of a pacer pulse is through the heart load and in a direction opposite to the flow during the period of the stimulating pulse. As such, the propensity toward iontrophoresis is reduced.

SUMMARY OF THE INVENTION

The foregoing advantages and features of the invention are achieved through the use of first and second bi-directional semiconductor switching devices, one being disposed in the lines connecting the heart lead terminals to the input circuit of the R-wave sensing amplifier and the other being disposed between the heart contacting lead terminals and the output of the voltage doubler circuit. Control means are provided such that the first switching means may be "closed" when the second switching means is "open" and vice versa. Hence, when the system is about to artificially stimulate the heart muscle through the generation of a pacer pulse, the first switching means is open and the second is closed. Similarly, when the system is looking for the occurrence of natural R-wave signals, the first switching means is closed and the second switching means is open.

A further semiconductor switching device is provided for controlling the actual generation of a pacer pulse. Specifically, first and second pairs of complementary symmetry transistors are connected in series between a voltage source and a point of fixed potential. The common collector electrodes of the first pair of complementary symmetry transistors are connected through the second switching means to the heart contacting electrode lead terminal whereas the common collector of the second pair of transistors is connected to one side of the voltage doubling capacitor. The other side of the voltage doubling capacitor is coupled through the second switching means to the other heart electrode lead terminal. The four base electrodes of the complementary symmetry transistors are connected through logic circuitry such that an artificial stimulating pulse may be of a predetermined amplitude or twice that amplitude. In either event, the charge removed from the voltage doubling capacitor during the generation of a pacer pulse is restored through the low impedance emitter to collector path of a semiconductor switch so that full recovery occurs within a relatively short interval which is less than the refractory period of the pacer system.

DESCRIPTION OF THE DRAWINGS

Further features and advantages of the invention will become apparent to those skilled in the art from the following detailed description of a preferred embodiment when considered in the light of the accompanying drawings in which:

FIG. 1 is a schematic diagram of an embodiment of the invention; and

FIG. 2 is a truth-table helpful in understanding the overall operation of the system of FIG. 1.

DESCRIPTION OF THE PREFERRED EMBODIMENT

Referring now to FIG. 1, there is indicated by numeral 10 a heart organ having electrodes 12 and 14 affixed to it. The electrodes are, in turn, coupled to the pacer output terminals 16 and 18 by means of flexible leads 20 and 22. The pacer system further includes a pulse generator 24, which is a circuit designed to produce output pulses at a predetermined rate in the absence of naturally occurring R-wave activity. When natural occurring R-waves are picked up by the heart contacting electrodes 12 and 14, a signal is produced for resetting the timing mechanism in the pulse generator 24, thereby inhibiting the generation of an artificial stimulating impulse. In the event that no reset pulse is produced, indicating an absence of normal heart activity, the pulse generator 24 completes its cycle and outputs control signals on the conductors 26, 28 and 30 in a manner which will be further described hereinbelow. Because various forms of circuits are available for implementing the pulse generator 24, it is deemed unnecessary to describe such a circuit in detail herein. This is especially the case in that the present invention does not relate to the design features of the pulse generator per se, but instead to a novel electronic switching circuit used to interface the pulse generator output to the heart contacting electrodes.

Conductor 26 is connected by a line 32 to a first input of a NAND gate 34 which has its second input tied to the conductor 28. The output from the NAND gate 34 is connected by a conductor 36 to the base electrodes of a first pair of complementary symmetry transistors, including the PNP transistor 38 and the NPN transistor 40. Transistors 38 and 40 have their collector electrodes connected in common at junction point 42. The emitter electrode of transistor 38 is adapted to be coupled to a source of positive potential $V_2$, whereas the emitter electrode of the transistor 40 is connected to a point of fixed potential, such as ground 44.

In a related fashion, the conductor 26 from the pulse generator 24 is connected to the base electrodes of a second pair of complementary symmetry transistors including PNP transistor 46 and NPN transistor 48. The collector electrodes of these last mentioned transistors are connected in common at a junction point 50 and the emitter electrode of the transistor 46 is connected to the $+V_2$ supply. The emitter electrode of transistor 48 is also connected to ground.

The output from the pulse generator 24, which appears on conductor 30, is coupled by way of a conductor 52 to the control terminal, C, of a COS/MOS bilateral transmission gate. When the control signal on the line 52 is of a first value, the bilateral switches are considered to be closed and present a low impedance across its in/out terminals. However, when the control signal on the line 52 is of a predetermined different value, the semiconductor switch device is in a high impedance (switch open) condition. Those desiring further information concerning the characteristics of a bilateral switch suitable for this purpose may refer to the Type CD 4066 B device manufactured and sold by the RCA Corporation, that device being fully described in a RCA publication entitled "COS/MOS Integrated Circuits" (Copyright 1978 by RCA Corporation).

A conductor 56 connects the junction point 50 to one side of the semiconductor switching device 54 and a conductor 58 joins the associated terminal to the pacer output terminal 16. A voltage doubling capacitor 60 is connected in series between the junction point 42 and a second in/out terminal of the switching device 54. The associated terminal of this device is coupled by a conductor 62 to the pacer output terminal 18.

A NAND gate 64 has its input connected to the junction point between conductors 30 and 52 and its output terminal is coupled by way of a conductor 66 to the control terminal, C, of a still further COS/MOS bilateral switch device 68. The device 68 may be identical to device 54 and is used to connect the pacer output terminals 16 and 18 to the inputs of a R-wave sensing amplifier 70. Specifically, terminal 16 is coupled to the inverting input terminal of the operational amplifier 70 through the switch device 68 and by way of capacitor 72 and resistor 74. The output terminals 18 of the pacer is coupled through the switch device 68 and by a capacitor 76 and a resistor 78 to the non-inverting input terminal of the operational amplifier 70. The operational amplifier 70 is arranged to produce at its output terminal 80 a signal which is proportional to the difference in voltage existing across its two input terminals. A feedback resistor 82 is used to control the gain of the amplifier 70 and a capacitor 84 may be used in a conventional fashion to stabilize the performance of the circuit.

The output signal from the amplifier 70 is applied to two further operational amplifiers 86 and 88 which are connected up to function as comparators. Specifically, the output signal appearing at terminal 80 is coupled through a capacitor 90 and a resistor 92 to the non-inverting input of the operational amplifier 86. The inverting input thereof is coupled through a resistor 94 to a point of fixed potential, e.g., ground. A voltage divider (potentiometer) 96 establishes a threshold and when the output signal from the amplifier 70 exceeds the predetermined threshold, comparator 86 produces a signal indicative of the fact that a received R-wave of a negative polarity has been detected. The comparator 88 is connected in a substantially identical relationship except that the input polarities are reversed with the non-inverting input connected through a resistor 98 to ground. Again, a potentiometer arrangement 100 is used to set the threshold.

The output signals from the comparators 86 and 88 are ORed together in circuit 102 and the resulting output is applied to the clock input terminal of a D-type flip-flop 104. When this flip-flop is set, it is indicative of the fact that a R-wave signal of either a positive or a negative polarity and of sufficient magnitude to exceed predetermined levels has been picked up by the heart contacting electrodes 12 and 14.

Now that the details of the construction of a preferred embodiment have been set forth in detail, consideration will be given to the mode of operation of this embodiment.

OPERATION

At the outset, let it be assumed that the patient is suffering from complete heart block so that the heart muscle must be continually paced with an externally applied electrical stimulating signal under control of the pulse generator 24 to ensure proper contraction of the heart muscle. Under this assumed condition, the pulse generator 24 will be made to output a control signal on line 30 which passes by way of conductor 52 to the bilateral switch device 54 placing it in its low impedance (switch on) condition. This same control signal on line 30 is inverted by NAND circuit 64 such that the signal on the control line 66 for the bilateral switch device 68 causes that device to be in its high impedance (switch off) condition. The voltage doubling capacitor 60 will be fully charged and will have the polarity indicated by the + polarity marker adjacent thereto.

The pulse generator 24 may be operated so as to cause a single amplitude impulse or a double amplitude impulse to be applied to the heart muscle. If the pulse generator 24 issues a high signal on line 26 and a low signal on line 28, the NAND gate 34 will output a high signal such that transistors 40 and 48 will be driven into their conduction state. Transistors 38 and 46 will remain off. A circuit path is thus established from ground 44 through the conducting transistor 40, the voltage doubling capacitor 60, the bilateral switch 54, and the conductor 62 to the pacer output terminal 18. The path continues through the lead arrangement 22 to the electrode 14 and through the heart load 10, electrode 12 and lead 20 to the pacer output terminal 16. From there the path continues through conductor 58, the bilateral switch device 54, the conductor 56 and the conducting transistor 48 to ground. Thus, only the potential difference existing across the voltage doubling capacitor 60 will be applied to the heart.

However, if the pulse generator 24 outputs high control signals on both lines 26 and 28, the NAND gate 34 will output a low signal such that transistors 38 and 48 are now conducting whereas transistors 40 and 46 are non-conducting. A circuit path is established from the source $+V_2$, through transistor 38, through the voltage doubling capacitor 60, the bilateral switch 54, the heart leads 22 and 20, the conductor 58, the bilateral switch 54, the conductor 56 and the conducting transistor 48 to ground. It can be seen that this path includes two voltage rises, namely the $V_2$ supply and the voltage on the capacitor 60. These voltages are connected in an aiding relationship such that twice the voltage $V_2$ is applied to the heart load 10.

When the pulse generator 24 is made to output low signals simultaneously on conductors 26 and 28, transistors 40 and 46 will be conductive whereas transistors 38 and 48 will be non-conductive. Under these conditions, and with the bilateral switch 54 conducting, the output terminals 16 and 18 will be at a potential difference of the battery potential $(+V_2)$ minus the voltage across the capacitor 60 due to the residual charge on the capacitor 60 after an imput pulse. Ths potential difference will cause current to flow, recharging the capacitor 60 back to the battery voltage.

Summarizing at this point, depending upon the state of the signals emanating from the pulse generator 24 at the terminals A and B thereof, the signal applied to the heart load 10 will be as indicated in the truth table of FIG. 2, i.e., either recovery, an undoubled output or a doubled output.

Following the generation of a paced pulse, the pulse generator 24 operates to turn on transistors 40 and 46 simultaneously for a relatively short period, which is substantially less than the refractory period established by the components in the pulse generator 24. With these two transistors conducting, a current path is established from the source $V_2$, through transistor 46, the conductor 56, the bilateral switch 54, the lead 20, the lead 22, conductor 62, the bilateral switch 54, the voltage doubling capacitor 60, the conducting transistor 40 to ground 44. Thus, the voltage doubling capacitor 60 is rapidly recharged to the voltage $V_2$ with the polarity sense as indicated by the + sign adjacent to it. The recharging operation takes place rapidly due to the fact that the only resistance in the charging circuit is the low resistance of the forward biased transistors 40 and 46, the low impedance of the conducting semiconductor bilateral switch 54 and the resistive component of the heart load. Because the bilateral switch 68 is essentially an open circuit, the input impedance of the sensing amplifier 70 is not a factor in determining the time constant of the recharging of the voltage doubling capacitor 60. It is to be further noted that because of the manner in which the complementary symmetry transistor pairs are rendered conductive during the voltage doubling capacitor recharge phase, the recharging current flows through the heart load 10 in a direction opposite to that produced by the stimulating pacer pulse. Hence, there is zero net charge flowing over a complete cycle and no opportunity for metallic ions to migrate from the electrodes 12 and 14 into the heart muscle (iontrophoresis).

When the patient is suffering from a heart abnormality which results in irregular heartbeat rates, the circuit of FIG. 1 may be made to operate in the so-called demand mode. In this mode, means are provided for detecting the occurrence of an R-wave produced by the depolarization of the heart muscle and if the amplitude of this R-wave signal exceeds predetermined thresholds, it will be recognized by the pacer as such and the pacer will be inhibited from generating a stimulating impulse during a predetermined period following the occurrence of the R-wave signal. Once this predetermined period has elapsed without the repeat occurrence of a further R-wave signal, the pacer system will function to again provide a stimulating pulse to the heart muscle to maintain an appropriate rhythm.

At a predetermined time following the termination of a pacer pulse, the pulse generator 24 outputs a signal on conductor 30 which opens the bilateral switch 54 and closes the bilateral switch 68. The system in FIG. 1 is now in a condition whereby it is "listening" for naturally occurring R-wave signals. Because of the high impedance afforded by the non-conducting bilateral switches 54, the circuitry to the left of that device does not act as a load upon the electrical impulses generated by the heart and, hence, substantially the entire potential difference picked up across the heart electrodes 12 and 14 becomes available for application to the input terminals of the sensing amplifier 70.

The R-wave signal is coupled through the conducting bilateral switch 68 and the impedances, including capacitors 72 and 76 and the resistors 74 and 78, to the complementing and non-complementing input terminals of the sensing amplifier 70. The operational amplifier 70 is connected to function as a differential amplifier, such that the signal appearing at its output terminal 80 is proportional to the difference in voltage existing across its input terminals. The amplitude of this output signal is compared to predetermined references in the comparator circuits 86 and 88 and, assuming that it is of sufficient amplitude, one of the comparators 86 or 88 will produce an output signal which is dependent upon whether a positive or a negative R-wave signal has been detected. In any event, the output signals from the comparators 86 and 88 are ORed together in circuit 102 and applied to the clock input terminal of a D-type flip-flop 104. Where the R-wave signal amplitude is above the prescribed threshold, then, the flip-flop 104 will be set on the leading edge of the comparator output pulse such that a control signal (the voltage at terminal "D") will become available at the Q-output terminal thereof. This signal may be fed back to the pulse generator 24 to act as a timer reset or may be used in still other fashions to perform other control functions well known to those skilled in the design and development of pacemaker products. For example, the output from the flip-flop 104 may be applied to a refractory timing circuit which would ensure that during a predetermined interval following a sensed beat that further outputs from the sense amplifier 70 occasioned by noise or otherwise would be ineffective to reset the timing mechanism in the pulse generator 24.

There has been described in detail a preferred embodiment of a novel switching arrangement for use in a cardiac pacer system which operates to perform a plurality of useful functions. Specifically, the circuit serves to isolate the sensing amplifier and threshold determining circuitry from the remainder of the system during a paced beat interval. Further, it operates to isolate the pulse generating circuitry and voltage doubling circuitry during a sensing interval. The novel switching circuitry further permits the system to apply a single amplitude or a double amplitude pacer pulse to the heart muscle. Finally, because of the manner in which the semiconductor switching devices are configured, the voltage doubling capacitor is recharged rapidly through a low impedance path following the termination of a pacer pulse, thus eliminating any problems that might be caused by the existence of a residual voltage difference across the voltage doubling capacitor at the conclusion of the system's refractory period.

For purposes of of illustration only and with no limitation intended, the switching arrangement of the present invention may be configured using the component values listed in the following table:

| Resistors | Capacitors |
|---|---|
| 74, 78—51 K | 60—22 uf |
| 79, 82—4.6 M | 72, 76—.15 uf |
| 92, 99—1 M | 84—560 pf |
| 94, 98—510 K | |
| 96, 100—2 M var. | 97, 99—.105 uf |
| Active Devices | Voltages |
| 38, 46—2 N 2907 | $V_1$ = 9 volts |
| 40, 48—2 N 2222 | $V_2$ = 3 volts |
| 43, 64—CD 4093 B | |
| 54, 68—CD 4066 B | |
| 70—CA 3078 | |
| 86, 88—CA 3140 | |
| 102—CD 4071 B | |
| 104—CD 4013 A | |

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself.

What is claimed is:

1. In a demand cardiac pacemaker of the type having a source of direct current voltage, a pulse generator connected to said source of direct current voltage for periodically producing triggering pulses in the absence of normal R-wave activity in the heart, a voltage doubler capacitor and a first semiconductor switching means responsive to said triggering pulses for selectively applying artificial stimulating pulses of a given amplitude to the heart by way of electrically conductive leads and electrodes, and a sensing amplifier exhibiting a relatively high input impedance and having input terminals coupled to said electrodes by way of said leads for receiving and amplifying heart depolarizing R-wave signals, the improvement comprising:
    (a) second semiconductor switching means coupled between said electrodes and said input terminals of said sensing amplifier and third semiconductor switching means coupled between said electrodes and said voltage doubler capacitor for disconnecting said electrodes from said input terminals and for connecting said voltage doubler capacitor to said electrodes during a predetermined interval following the application of one of said triggering pulses to said first semiconductor switching means; and
    (b) further semiconductor switching means selectively exhibiting a low impedance for coupling said source of direct current voltage through said heart to said voltage doubling capacitor for a relatively short predetermined time following termination of said one of said triggering pulses for rapidly restoring the charge on said voltage doubling capacitor.

* * * * *